United States Patent [19]

Morse et al.

[11] Patent Number: 4,932,114

[45] Date of Patent: Jun. 12, 1990

[54] METHOD OF MAKING A ROTATING ADAPTER FOR CATHETERS

[75] Inventors: Phillip H. Morse; Cynthia L. Morris, both of Glens Falls; Ronald L. West, Fort Ann, all of N.Y.

[73] Assignee: North American Instrument Corp., Glens Falls, N.Y.

[21] Appl. No.: 219,300

[22] Filed: Jul. 14, 1988

[51] Int. Cl.$^5$ .............................................. B23P 11/00
[52] U.S. Cl. ...................................... 29/443; 29/511; 264/242; 264/249; 285/281; 285/331; 285/382; 604/905
[58] Field of Search ................ 29/437, 439, 440, 443, 29/508, 509, 510, 511, 434, 243.5, 243.57, 243.58, 515, 516; 264/249, 242; 285/275, 278, 280, 281, 331, 382; 604/240, 283, 905

[56] References Cited

U.S. PATENT DOCUMENTS

| 574,236 | 12/1896 | Blackburn | 285/320 |
|---|---|---|---|
| 964,238 | 7/1910 | Goss | 285/320 |
| 1,209,374 | 12/1916 | Andreolli | 285/320 |
| 1,241,654 | 10/1917 | Osgood | 29/511 |
| 1,797,418 | 3/1931 | Hothersall | 29/511 |
| 1,804,284 | 5/1931 | Smith | 29/511 |
| 2,793,912 | 5/1957 | Krohm | 285/281 X |
| 2,876,535 | 3/1959 | Ray | 285/281 |
| 3,042,965 | 7/1962 | Gray et al. | 425/392 |
| 3,644,874 | 2/1972 | Hutter | 29/443 X |
| 3,768,476 | 10/1973 | Raitto | 285/331 X |
| 4,123,091 | 10/1978 | Cosentino et al. | 285/39 |
| 4,254,773 | 3/1981 | Waldbillig | 128/348 |
| 4,392,836 | 7/1983 | Sugawara | 464/52 |
| 4,405,312 | 9/1983 | Gross et al. | 604/29 |
| 4,542,922 | 9/1985 | Grossauer | 285/320 |
| 4,687,235 | 8/1987 | Stoll | 285/281 |
| 4,714,278 | 12/1987 | Gassmann et al. | 285/331 X |

FOREIGN PATENT DOCUMENTS 1067286 5/1967 United Kingdom ................ 285/281

Primary Examiner—Joseph M. Gorski
Assistant Examiner—Andrew E. Rawlins
Attorney, Agent, or Firm—Kenyon & Kenyon

[57] ABSTRACT

A two-piece adapter for rotatably connecting two fluid transport members, the adapter including a stem for one of the members, and a connector (which may be for example a Luer connector) for the other member. The connector has a collar which is wrapped around the flange to capture the stem. The collar is deformed to wrap around the flange after the flange and the collar are joined. Preferably the adapter is made of a plastic, transparent material.

21 Claims, 3 Drawing Sheets

METHOD OF MAKING A ROTATING ADAPTER FOR CATHETERS

BACKGROUND OF THE INVENTION a. Field of Invention

This invention pertains to an adapter which may be used to connect a tubular member such as a catheter to another member in a manner which allows the tubular member to rotate around its longitudinal axis, and more particularly this invention pertains to a two-piece rotating adapter. The invention also pertains to a method of making the adapter.

b. Description of the Prior Art

In many technical fields it is desirable to have an adapter for coupling two members in such manner that they are rotatable with respect to each other around a common longitudinal axis. For example, during many surgical procedures the distal end of a catheter is inserted along a tortuous path into the body of the patient by rotating the catheter around its longitudinal axis. The catheter's proximal end is connected to a stationary device for injecting and/or withdrawing fluids through the catheter to and from the body. In such applications a rotating adapter is required for coupling these elements to permit rotation of the distal end with respect to the proximal end.

A prior art rotating adapter 10 is shown in FIG. 1. This adapter had three parts: a stem 12, having a flange 13, a collar 14 rotatably mounted on the stem 12, and an insert 16 spot-welded to the collar 14. An O-ring 18 was used to form a seal between the insert 16 and the stem 12. The manufacture of this type of adapter is expensive and very time consuming. First the collar has to be made and positioned on the stem in a first direction because its inside diameter is smaller than the stem head 20. After the collar is positioned over the stem, the insert 16 must be inserted into the collar from a second direction. The collar and insert must be mounted on the stem from opposing directions, and the completed assembly must usually be attached to a final product, e.g. a manifold, syringe, or the like.

A two-piece swivel coupling has been proposed by Waldbilig in U.S. Pat. No. 4,254,773. In this coupling, the stem is provided with a flexible lip 48 which snaps over a flange 31 of body 21. However, this device is also expensive, and difficult to assemble.

OBJECTIVES AND SUMMARY OF THE INVENTION

In view of the abovementioned disadvantages of the prior art, it is an objective of the present invention to provide a rotatable adapter which is reliable and yet can be made inexpensively.

Another objective of the invention is to provide an adapter with a minimal number of parts.

Another objective of this invention is to provide a two-piece rotating adapter that has the feel of an adapter of the three-piece design.

A further objective of the invention is to provide a method of making a two-part rotatable adapter which is inexpensive, yet reliable.

Other objectives and advantages of the invention shall become apparent from the following description. Briefly the present invention provides a rotatable adapter comprising two pieces: a stem having a flange, and a connector having a collar disposed concentrically on the flange, with a portion of the collar capturing the flange. The connector also has a section which is used to connect the adapter to a second member. This second section may include for example a Luer connector. A toroidal cavity is formed between the stem and the connector for housing an O-ring used to seal the adapter preventing leakage of fluid passing therethrough. Preferably, the adapter is made of a plastic material which is strong enough to withstand large internal pressures, and which can be softened by the application of heat. Preferably the plastic material is transparent so that fluids passing therethrough may be inspected easily for air bubbles or other undesirable impurities.

The adapter is made by first forming the stem and the connector by any well known means such as injection molding. The connector is mounted on the stem with the O-ring disposed in its cavity and the collar overlapping the flange. The collar is then heated and while connector is rotated and heated to soften it, its end is softened and deformed to wrap around the flange thereby capturing it. Heat may be applied to the collar by forced hot air.

DETAILED DESCRIPTION OF THE INVENTION

Figure 1:
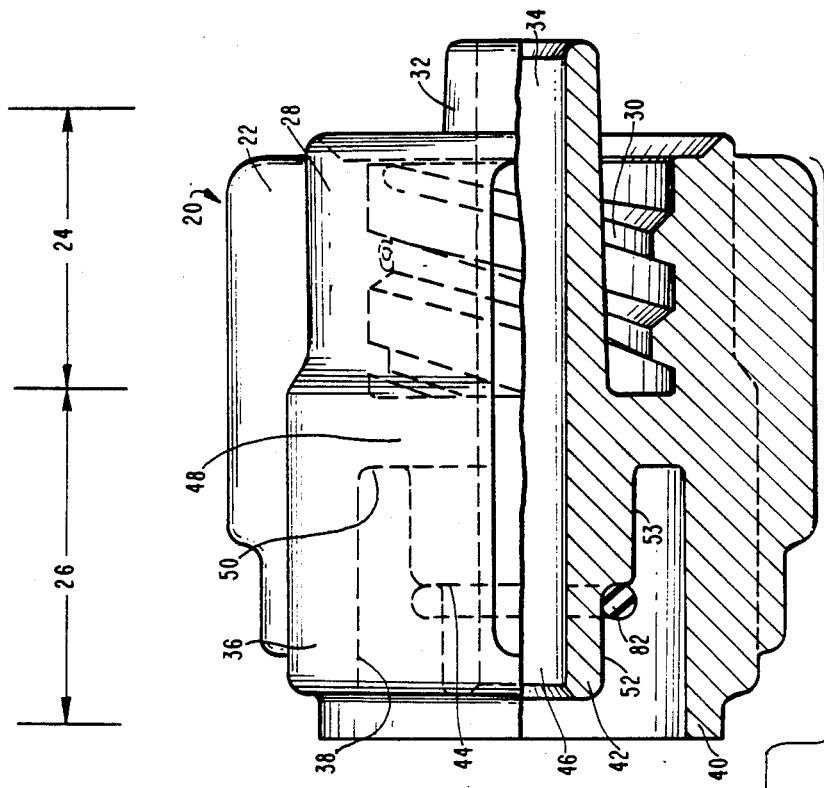
FIG. 1 shows a side cross-sectional view of a prior art three-piece rotatable adapter.
Figure 1:
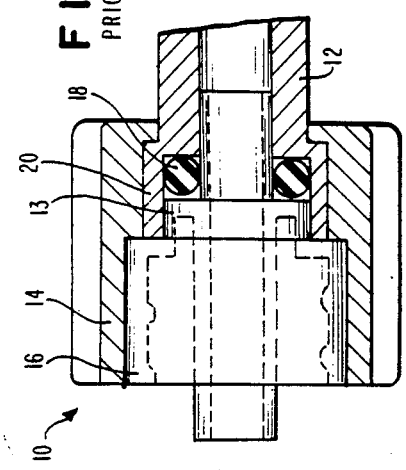
Figure 2:
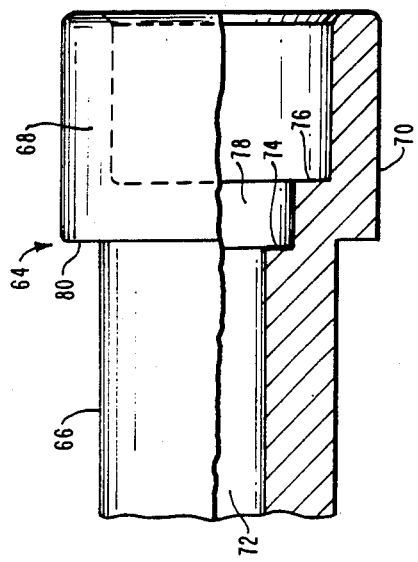
FIG. 2 shows side cross-sectional view of a rotating adapter constructed in accordance with this invention prior to final assembly.

A rotating adapter constructed in accordance with this invention includes two parts, a connector and a stem. The connector 20, shown in FIG. 2 prior to assembly, is generally cylindrical and is provided on its outer wall with a plurality of longitudinal fins 22. These fins are used to grasp the connector and turn it with respect to the stem, or to hold the adapter while another tube is inserted into it. The connector consists of two axially spaced sections 24 and 26. Section 24 is provided to mate with another tube (or any other fluid transport means). In FIG. 2, section 24 is formed to mate with a Luer connection and for this purpose it is provided with an outer collar 28 which on its inner surface is threaded as at 30. Section 24 also has an inner tapered extension 32 coaxially disposed with respect to outer collar 28. Extension 32 is provided with a longitudinal hole 34.

Section 26 is also provided with an outer collar 36. This collar 36 has an inner wall 38 which is substantially cylindrical and extends longitudinally along the section. The end of collar 36 opposite section 24 is narrowed to form a ring 40. The purpose of this ring is described below. Section 26 also has an inner cylindrical extension 42 coaxial with collar 36. Extension 42 has a circular shoulder 44 and an inner longitudinal hole 46. Shoulder 44 divides extension 42 into two axially spaced segments 52 and 53. Segment 52 has a narrower outer diameter than segment 53. Holes 34 and 46 are aligned and continuous to form a fluid path. Section 26 further includes a disk-shaped wall 48 which supports extensions 32 and 42 as shown. Wall 48, collar 36 and extension 42 cooperate to form a circular groove 50.

Stem 64, also shown in FIG. 2 comprises a tube 66 terminated in a flange 68 having an outer cylindrical wall 70. Tube 66 may be the extension of another device such as a manifold, a syringe or even another tube. Tube 66 has a longitudinal hole 72 which has approximately the same diameter as holes 34 and 46, and at the interface with flange 68, it is terminated by two inner shoulders 74 and 76 thereby defining a circular depression 78 therebetween. The diameter of depression 78 matches the outer diameter of segment 52 while the inner diameter of flange 68 matches the outer diameter of segment 53. The longitudinal length of portion 52 is larger than the axial depth of depression 78. At the end nearest to tube 66, flange 68 has an external shoulder 80. The longitudinal length of outer wall 70 on the flange matches the corresponding length of inner wall 38, excluding ring 40. Thus the two longitudinal walls are complementary to prevent lateral play between the connector and the stem.

In order to insure that no leakage occurs between the two pieces of the adapter, an O-ring 82 is provided as described below.

Figure 4:
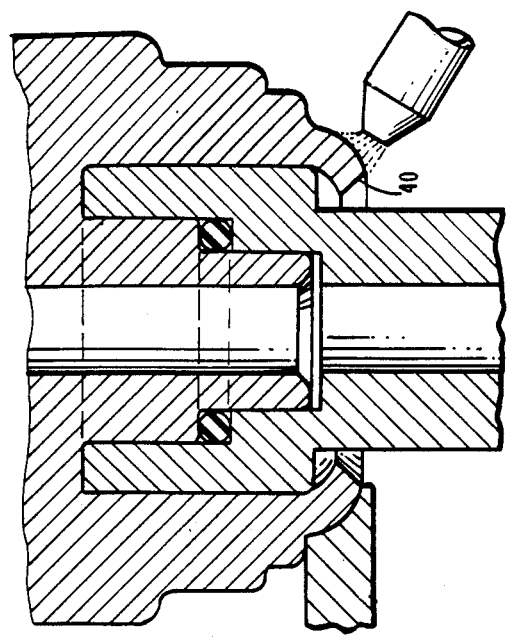
FIGS. 3 and 4 show the steps required to assemble the adapter of FIG. 2.
Figure 3:
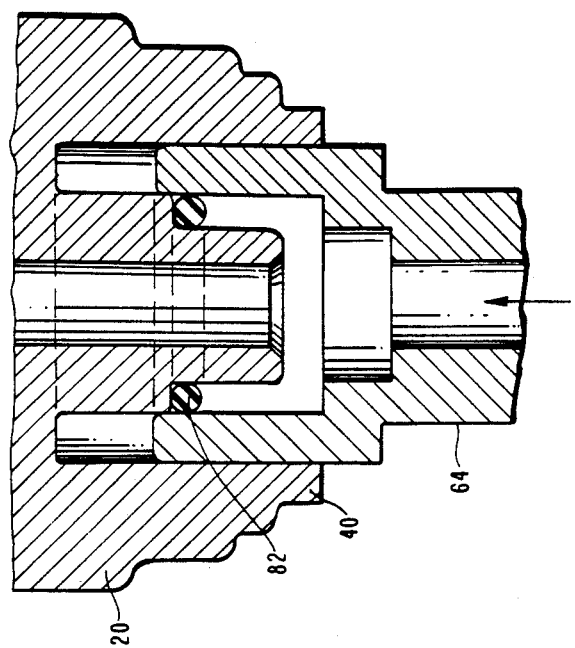

The two pieces of the adapter are assembled as follows. First, the connector is aligned with section 26 facing stem 64 and the O-ring 82 disposed on adapter portion 52. The two pieces are joined in an axial engagement with flange 68 disposed in groove 50 with longitudinal cylindrical walls 38 and 70 contacting each other. Thus the connector and stem are constructed and arranged such that they fit together snugly but can still rotate with respect to each other around a common axis. Importantly, when flange 68 reaches its final position in which it contacts wall 48, segment 52 is partially disposed in depression 70, however an annular space is formed between shoulders 76 and 44 to house O-ring 82. In this final position ring 40 extends past shoulder 80 on stem 64. In order to complete the assembly of the adapter, the connector is now partially deformed by bending ring 40 to wrap around shoulder 80 thereby capturing the stem. The assembly of the adapter is illustrated in FIGS. 3 and 4. In FIG. 3 the flange is inserted into the collar. In FIG. 4, ring 40 is molded around the flange.

In effect, the connector 20 has a cylindrical annular cavity terminated at its axial ends by wall 48 and ring 40 respectively for the rotatable engagement of the flange 36. Due the interaction between the outer surface 70 of the flange, and the inner surface 38 of the collar, the connector and the stem are aligned in their axial positions and resist lateral forces. The two ends of the cavity, i.e. the wall 48, ring 40, and groove 50 form a very stable seat for the flange and further provide a barrier for any liquid from the axial holes of the adapter. It should also be appreciated that ring 40 is wrapped over the shoulder 80 of the flange during the final assembly. Therefore the annular cavity in the collar is matched automatically to the shape of the flange independently of any dimensional variations of the flange.

The adapter described herein may have for example the following dimensions (in inches):

| | |
|---|---|
| Overall length of connector (before ring 40 is deformed) | 0.62 |
| Axial length of ring 40 | 0.05 |
| Thickness of ring 40 (before deformation) | 0.03 |
| Length of section 24 | 0.27 |
| Length of walls 38 and 70 | 0.24 |
| Diameter of Section 26 (Excluding fins 22) | 0.49 |
| Diameter of flange 68 | 0.335 |

Although the adapter described herein can be made of any suitable material, it is preferred that it be made of a plastic material such as a rigid engineering resin, such as compound RX 31112 or Malcrolon RX 2548 available from Mobay Chemical Company of Pittsburgh, Pennsylvania, or Lexan HP-111 available from General Electric Company. It was found that these materials, and especially RX 31112, are particularly suitable for making the adapter because they have the necessary mechanical properties, are inexpensive, and readily available off-the-shelf. Furthermore, the two pieces shown in FIG. 2 are easily made by well known molding techniques, and with a high degree of accuracy and dimensional stability. It was also found that when made from such materials the connector can be easily deformed by the application of heat to the ring 40. Another advantage of these materials is that they are colorless and highly transparent. Therefore, during a surgical procedure, the fluid flowing through the adapter can be visually inspected for air bubbles or other undesirable elements.

Figure 5:
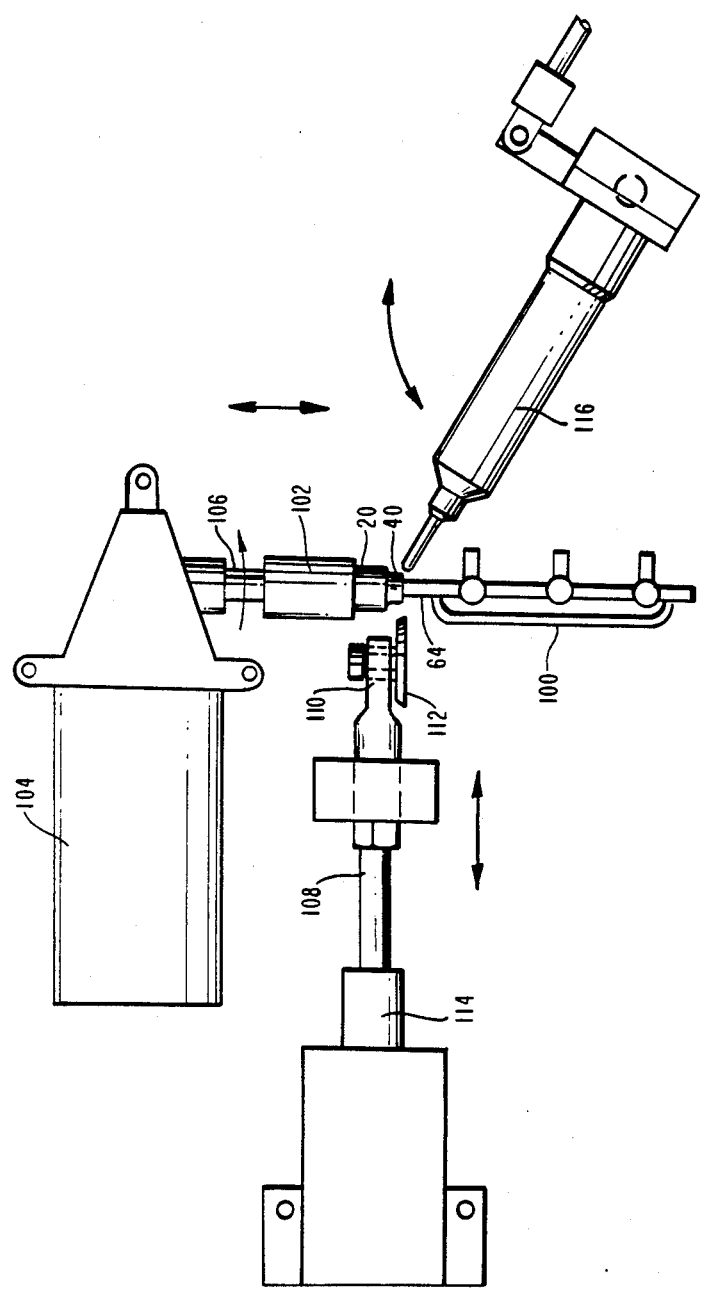
FIG. 5 shows an apparatus for completing the assembly of the adapter of FIG. 2.

An apparatus for assembling the parts to form the adapter is shown in FIG. 5. In this Figure, the adapter is connected to a specific device used in surgical procedures such as a MORSE ® manifold 100. The manifold has an extension which terminates with stem 64. After the stem has been inserted into connector 20, the connector and the manifold are secured into the position shown in FIG. 5. (The means for securing the manifold have been omitted for the sake of clarity.) The apparatus includes a sleeve 102 which may be selectively slipped over the adapter. The sleeve 102 is rotatable around its axis by a motor 104 through an extension arm 106. The apparatus also includes a horizontal arm 108 terminating in a socket 110 which holds a forming wheel 112. The forming wheel is rotatable around a horizontal axis passing through the socket. Arm 108 is attached to a cylinder 114 provided for selectively moving the arm and the forming wheel toward and away from the adapter. The apparatus of FIG. 5 also includes a nozzle 116 for blowing a hot gas toward the adapter.

The apparatus of FIG. 5 operates as follows. After the manifold 100 is secured with the adapter parts in the position shown in FIG. 5, the sleeve 102 engages the connector, with the ring 40 extending past the sleeve 102. The sleeve is then rotated by the motor 104, and the nozzle 116 moves into position to heat the ring 40. As the ring 40 is heated by hot gas from nozzle 116, the forming wheel 112 is moved horizontally to contact and press the ring in a radial direction into its final shape in which it overlaps the shoulder 80, and captures the stem 64. Importantly, while the connector 20 is continuously rotated by sleeve 106, the stem remains stationary. In this way it is insured that the connector is not tacked to the stem. Thus after the deformation of the connector is complete, the connector is still fully rotatable with respect to the stem. When using the disclosed engineering elastics, the hot gas preferably has a temperature of about 445–470 degrees F. The sleeve may be rotated at a speed in the range of 10–60 RPM preferably to form the ring in about 2.5–3.5 seconds.

It is clear from the above description that the rotating adapter described herein is easy and inexpensive to make, yet it has many advantageous features. For example, the longitudinal walls 38 and 70 cooperate to resist any lateral forces on the adapter (i.e. forces at an angle with respect to its longitudinal axis). The adapter has also been found to be operative at pressures of over 1600 p.s.i. Numerous modifications may be made to the device, and the method of producing the same without departing from its scope as defined in the appended claims.

We claim:

1. A method of making a two-piece adapter for rotatably connecting a first member to a second member comprising the steps of:
    (a) forming a hollow stem on said first member, said stem having a cylindrical flange with a flange outer diameter, said flange having a first flange end and a second flange end, said first flange end defining an external shoulder;
    (b) forming a plastic connector for said second member, said connector having a cylindrical collar with an inner diameter substantially equal to said flange outer diameter, said collar having a length equal to an axial length of said flange and having a first end terminating in a capture ring and a second end having a wall for abutting said second flange end;
    (c) inserting said stem into said connector until said second flange end abuts said collar wall; and
    (d) deforming said ring over said first flange end while rotating said first and second members with respect to each other to rotatably capture said stem.

2. The method of claim 1 further comprising heating said collar while said collar is deformed.

3. The method of claim 2 wherein said deforming step comprises contacting a forming wheel to said ring to press said ring in a radial direction.

4. The method of claim 1 wherein said plastic is a rigid engineering resin.

5. The method of claim 1 wherein said connector and stem are made of a transparent material.

6. The method of claim 1 wherein said connector is made of a polycarbonate.

7. A method of making a high pressure rotating adapter for medical applications comprising the steps of:
    (a) forming a hollow tubular stem extending from a first member, said stem having a cylindrical flange disposed at one end thereof which includes two inner shoulders which define an annular depression within the hollow tubular stem, said flange having a first flange end and a second flange end, said first flange end defining an external shoulder;
    (b) forming a plastic connector having a first and a second section on a common axis, said first section having a female Luer fitting at one end thereof, said second section having an adapter portion for nesting in the annular depression of said flange and having a cylindrical outer collar, said outer collar having a first end terminating in a capture ring, and a second end having a wall for abutting said second flange end;
    (c) disposing an O-ring on said adapter portion;
    (d) inserting said stem into said connector until said second flange end abuts said collar wall such that said O-ring seals said stem and said connector; and
    (e) deforming said capture ring radially over said first flange end while rotating said first and second members with respect to each other to rotatably capture said stem.

8. The method of claim 7 wherein said connector is made of a rigid engineering resin.

9. The method of claim 7 wherein said connector is made of a polycarbonate.

10. The method of claim 7 further comprising heating said ring while said ring is deformed.

11. The method of claim 10 wherein said deforming step comprises contacting a forming wheel to said ring to press said ring in a radial direction.

12. A method for making a two-piece plastic adapter for rotatably connecting a first member to a second member, comprising the steps of:
    (a) forming a cylindrical flange having a first flange end and a second flange end on the first member, the first flange end defining a shoulder;
    (b) forming a cylindrical cavity in the second member defined by an inner surface of complementary shape to the flange, the cylindrical cavity having a first inner surface end including a capture ring extending therefrom and a second inner surface end for abutting the second flange end;
    (c) inserting the cylindrical flange into the complementary shaped cavity until the second flange end abuts the second inner surface end; and
    (d) deforming the capture ring while rotating the first and second members with respect to each other to engage the shoulder so that the first and second members are rotatably connected.

13. The method of claim 12 further comprising heating said capture ring while said capture ring is deformed.

14. The method of claim 13 wherein said deforming step comprises contacting a forming wheel to said capture ring to press said capture ring in a radial direction.

15. The method of claim 12 wherein said adapter is made of a rigid engineering resin.

16. The method of claim 12 wherein said adapter is made of a polycarbonate.

17. A method of making a high pressure rotating adapter for medical applications comprising the steps of:
    (a) forming a tubular stem extending from a first member, said stem having a flange disposed at one end thereof which includes two inner shoulders which define an annular depression within the hollow stem, said flange having a first flange end and a second flange end, said first flange end defining an external shoulder;
    (b) forming a plastic connector having a first and a second section on a common axis, said first section having a female Luer fitting at one end thereof, said second section having an adapter portion for nesting in the annular depression of said flange and having a cylindrical outer collar, said outer collar having a first end terminating in a capture ring and a second end with a wall for abutting said second flange end;
    (c) disposing an O-ring on said adapter portion;
    (d) inserting said stem into said connector until said second flange end abuts said collar wall;
    (e) engaging said connector with a rotatable sleeve, with said ring extending out of said sleeve;
    (f) rotating said sleeve to rotate said connector while said stem remains stationary;

(g) heating said ring;
(h) contacting a forming wheel to said ring to press said ring in a radial direction over said first flange end to rotatably capture said stem.

18. The method of claim 17 wherein said connector is made of a rigid engineering resin.

19. The method of claim 17 wherein said connector is made of a polycarbonate.

20. The method of claim 17 wherein said heating comprises applying hot gas to said ring.

21. The method of claim 17 wherein said sleeve is rotated at a speed of from 10 RPM to 60 RPM for about 2.5 to about 3.5 seconds and said heating is at a temperature of from about 445 degrees F. to about 470 degrees F.

* * * * *